United States Patent [19]

Boy et al.

[11] 4,177,208

[45] Dec. 4, 1979

[54] PROCESS FOR PREPARING SULPHONIC ACIDS AND SULPHONATES

[75] Inventors: Aristide Boy; Henri Galy, both of Pau; Raoul Ivaldi, Orthez; Hubert Passedroit, Gan, all of France

[73] Assignee: ATO Chemie, Paris, France

[21] Appl. No.: 895,795

[22] Filed: Apr. 12, 1978

Related U.S. Application Data

[63] Continuation-in-part of Ser. No. 732,120, Oct. 13, 1976, abandoned, which is a continuation-in-part of Ser. No. 645,092, Dec. 29, 1975, abandoned, which is a continuation of Ser. No. 507,246, Sep. 18, 1974, abandoned, which is a continuation of Ser. No. 169,145, Aug. 4, 1971, abandoned.

[30] Foreign Application Priority Data

Aug. 7, 1970 [FR] France .................................. 70.29211
Jul. 22, 1971 [FR] France .................................. 71.26794

[51] Int. Cl.$^2$ ..................... C07B 13/00; C07C 143/02
[52] U.S. Cl. ............................ 260/504 S; 260/513 R
[58] Field of Search .......................... 260/504 S, 513 R

[56] References Cited

FOREIGN PATENT DOCUMENTS 1358095  6/1974  United Kingdom ..................... 260/504

Primary Examiner—Alan Siegel
Attorney, Agent, or Firm—Burgess, Ryan and Wayne

[57] ABSTRACT

A process for separating sulphonic acids from a paraffin sulphonic acid solution containing in addition to the paraffin sulphonic acids, sulphonic acid, water and optionally non-sulphonated paraffins by mixing the solution with a slightly polar alcohol having solubility in water of less than 7 percent to form an aqueous phase and an organic phase, separating the phases, neutralizing the organic phase and recovering the paraffin sulphonic acids from the neutralized organic phase.

10 Claims, No Drawings

PROCESS FOR PREPARING SULPHONIC ACIDS AND SULPHONATES

This application is a continuation-in-part of our co-pending application Ser. No. 732,120, filed Oct. 13, 1976 now abandoned, which was a continuation-in-part of application Ser. No. 645,092 filed on Dec. 29, 1975, now abandoned, which, in turn, was a continuation of application Ser. No. 507,246, filed on Sept. 18, 1974, now abandoned, which was a continuation of application Ser. No. 169,145 filed Aug. 4, 1971 now abandoned.

The present invention concerns an improved process for separating paraffin sulphonic acids contained in an untreated sulphonic solution which also includes, in addition to these acids, sulphuric acid, water and non-sulphonated paraffins.

Certain sulphonic acids derived from hydrocarbons, and more specifically those obtained from linear paraffins, are subject to deterioration as a result of biological action, even at low temperature.

This makes such products particularly suitable for use as detergents, since they can be discharged into rivers or sea without causing any serious pollution of the aqueous environment that could harm aquatic flora and fauna.

These paraffin sulphonic acids can be produced by various methods, and in particular by the "sulphoxidation method", in which sulphur dioxide and oxygen are made to act simultaneously on paraffins, in particular linear paraffins, in the presence of photoactive radiations. A suitable amount of water is added, to extract the paraffin sulphonic acids out of the reaction mixture.

The untreated sulphonic solution, extracted from the reaction zone, which contains the paraffin sulphonic acids produced, sulphuric acid, water and a certain amount of paraffins which have not reacted, is treated in order to recover the sulphonic acids.

An existing method of performing this separation involves the addition to the reaction mixture from the sulphonation reactor of a polar light organic solvent that will not mix with paraffins such as methanol, ethanol or light esters, to bring about separation of the solution into a hydrocarbon phase and a paraffin-free aqueous organic phase containing the sulphonic acids and sulphuric acids in solution, and then neutralization of the aqueous-organic phase by means of an alkaline hydroxide, to separate out the sulphuric acid in the form of sulphate, which is removed by filtration, and finally, treatment of the aqueous-organic solution with an alkaline salt, in order to salt out the sulphonic acids or/and sulphonates.

This process has proved uneconomical, because of the high consumption of alkaline hydroxide needed to convert the sulphuric acid into sulphate, and the serious losses of sulphonates or sulphonic acids that occur during filtration of the sulphate. In addition, use of the process on an industrial scale, which, to be economic, requires continuous filtration of the sulphate, involves difficulties arising from the possibility of frequent clogging of the filters.

Another existing process consists of removing part of the sulphuric acid contained in the reaction mixture from the sulphonation reactor before extracting the paraffin sulphonic acids. The process involves rapid evaporation of the reaction mixture by heating up to 180° C., causing separation of the mixture into an upper layer containing the paraffins and sulphonic acids, and a lower layer of aqueous sulphuric acid which is then removed.

This process is not completely satisfactory either, because the heating required for evaporation of the reaction mixture causes fairly marked deterioration of the sulphonic acids, affecting the quality of the final product.

The present invention provides a remedy for the drawbacks of these existing processes, by making it possible to separate substantially all of the sulphuric acid from the paraffin sulphonic acids without the formation of an alkaline sulphate, and deterioration of the sulphonated products. Additionally, the invention provides a method for the recovery of the sulphonic acids as alkaline sulphonates in the form of free-flowing, substantially anhydrous and non-caking particles.

The process according to the invention for separating sulphonic acids from a paraffin sulphonic acid solution containing in addition to said paraffin sulphonic acids, sulphuric acid, water and optionally, non-sulphonated paraffins, comprises the following steps:

(a) admixing with the paraffin sulphonic acid solution at least one slightly polar alcohol selected from the group consisting of aliphatic and cycloaliphatic alcohols containing at least 5 carbon atoms, having a solubility in water less than 7% by weight and which forms an azeotrope with water, thereby forming a mixture having an organic phase containing paraffin sulphonic acids dissolved therein and an aqueous phase containing sulphuric acid.

(b) separating said organic phase from said aqueous phase, (c) neutralizing said separated organic phase by admixture with a composition selected from the group consisting of alkali metal hydroxides, alkali metal carbonates, alkaline earth metal oxides, alkaline earth metal hydroxides, alkaline earth metal carbonates and mixtures thereof thereby converting the sulphonic acids present in said separated organic phase into sulphonates. The ratio of the amount of water to the amount of slightly polar alcohol in said neutralized phase, preferably controlled or adjusted if necessary so that said ratio is at most equal to the corresponding ratio for the azeotrope which forms between water and the slightly polar alcohol, then (d) removing the volatile components from the neutralized organic phase to recover the sulphonates under temperature and pressure conditions to maintain said sulphonates in a molten state. The molten sulphonate product can be solidified and comminuted into particulate form or can be solidified in particulate form.

The slightly polar alcohols useful in the process according to the present invention are selected from the group consisting of aliphatic or cycloaliphatic alcohols containing at least five carbon atoms, which have a solubility in water less than 7% by weight and which form an azeotrope with water. Among these compounds, those containing from 5 to 12 carbon atoms and having a solubility in water less than 5% by weight are preferred. In particular the slightly polar alcohols useful in the process according to the invention can be selected from the group consisting of alkanols and cycloalkanols, which have at least five carbon atoms and preferably from five to 12 carbon atoms and which have a solubility in water less than 7% by weight and preferably less than 5% by weight.

The alkanols and cycloalkanols include for example 1-pentanol, 1-hexanol, 1-heptanol, 1-octanol, 1-decanol, 1-dodecanol, 2-ethyl 1-butanol, 2-methyl 1-pentanol, 2-ethyl 1-hexanol, 2,6-dimethyl 4-heptanol, 3-ethyl 1-hexanol, 2,7-dimethyloctanol, 2-octanol, cyclohexanol, cyclooctanol, mixtures of these alcohols and the like.

The amount of slightly polar alcohol or mixture of such alcohols added to the sulphonic acid solution in order to bring about separation of the sulphonic acid, generally ranges from 10 to 150 parts by weight to 100 parts by weight of the sulphonic acid solution, and preferably from 30 to 100 parts by weight to 100 parts by weight of said solution.

When the sulphonic acid solution contains some unreacted paraffins, said paraffins may be removed from the mixture containing the sulphonic acids before or after separation of the sulphuric acid, by adding a strongly polar liquid, such as methanol, ethanol, low molecular weight carboxylic acids, acetone, sulphoxides, which dissolves in water and does not mix with the paraffins, to cause them to salt out.

The mixture containing the sulphonic acids to which the strongly polar liquid is added can be the untreated sulphonic acid solution, if the paraffins are removed before separation of the sulphuric acid, or the organic phase containing the sulphonic acids in solution in the slightly polar solvent, if removal of the paraffins takes place after separation of the sulphuric acid.

The amount of strongly polar liquid added to the mixture containing the sulphonic acids generally ranges from 10 to 90% of the weight of the mixture containing the sulphonic acid and is preferably equal to about 60% of this weight.

When the unreacted paraffins are removed from the untreated sulphonic acid solution, the strongly polar liquid is usually separated from the substantially paraffin-free sulphonic solution before treatment with the slightly polar alcohol.

According to the invention the organic phase containing the paraffin sulphonic acids dissolved in the slightly polar alcohol is neutralized and the ratio of the amount of water to the amount of slightly polar alcohol in said neutralized phase is controlled so that said ratio is at most equal to, and preferably less than the corresponding ratio for the azeotrope which forms between water and the slightly polar alcohol. The neutralized organic phase is heated to remove the volatile components therefrom and to obtain the sulphonates as a molten mass which can be cooled and comminuted into particles.

Suitable neutralizing agents include hydroxides and carbonates of alkali-metals, particularly sodium and potassium and oxides, hydroxides and carbonates of alkaline-earth metals, particularly calcium, or mixtures of the foregoing and the like.

These agents may be used in solid form, or in alcoholic or aqueous solutions. The neutralizing agents are generally used in proportions at least sufficient to neutralize all the sulphonic acids, and preferably in a slight excess of the agent in relation to the stoichiometric proportion.

As previously indicated, while neutralizing the organic phase or after the neutralization has been performed but before the volatile solvents are separated from the neutralized phase, the ratio of the amount of water to the amount of slightly polar alcohol in the neutralized phase is preferably adjusted so that the value of said ratio is at most equal to, and preferably less than the value of the corresponding ratio for the azeotrope which forms between water and the slightly polar alcohol. The adjustment can be performed by merely determining the water content of the neutralized organic phase and if the determined content is higher than the content which corresponds to the azeotrope between water and the slightly polar alcohol, a sufficient quantity of slightly polar alcohol is added to the neutralized organic phase so that its water content is brought back to a value which does not exceed the content for said azeotrope. It is also possible to adjust the ratio of the amount of water to the amount of slightly polar alcohol in the neutralized organic phase by determining the water content of the organic phase to be neutralized and then adding to said phase the neutralizing agent in the most appropriate form, namely in solid form or as a solution of suitable concentration in the slightly polar alcohol or in water so that the total water content of the neutralized solution, which includes the water content of the organic phase to be neutralized together with the water content resulting from the neutralization reaction and possibly the water content from the added water if an aqueous solution of neutralizing agent is used, is at most equal to, and preferably less than the water content for the azeotrope. This control of the ratio of the amount of water to the amount of slightly polar alcohol in the neutralized phase, performed either during the neutralization or after carrying out the neutralization, insures that a complete removal of the water is obtained during the evaporation step of the neutralized organic phase and accordingly that a substantially anhydrous sulphonate mass is produced.

Evaporation of the neutralized organic phase is carried out under pressure and temperature conditions that will ensure that the sulphonate is molten. The operation is generally performed at atmospheric pressure, though it is possible to work under a vacuum of varying force. The temperature required is dependent upon the melting point of the sulphonate.

In a variant involving the treatment of the organic solution of the sulphonic acids in the slightly polar alcohol from which the paraffins have been removed by treatment with a strongly polar liquid after separation of the sulphuric acid, the polar liquid is recovered by distillation after the neutralization step and before evaporation of the slightly polar alcohol. The strongly polar liquid is generally water soluble.

The alkali-metal or alkaline earth metal sulphonate collected in molten form after evaporation of the volatile solvents from the neutralized organic phase is substantially free from water, slightly polar alcohol and unreacted paraffins. It can easily be converted into a free-flowing, practically anhydrous and non-caking white powder.

This powder can be handled easily and is particularly well-adapted to pneumatic conveyance. It can be stored without difficulty and is easily incorporated into detergents sold commercially in powder form.

The particle size of this powder can vary widely, depending on the use to which it is to be put. For normal purposes, it is preferably between 40 and 600 microns.

The powder may be prepared by any process enabling a powder of given particle size to be obtained from a molten mass. The mass of molten sulphonate can be solidified in the form of flakes, for example, and the flakes ground to the particle size required in a suitable device, such as a disintegrator with blades rotating at high speed.

The mass of molten sulphonate can also be atomized in a current of cold gas, inert in relation to the sulphonate, such as an air current. To achieve this atomization, the molten sulphonate may be injected under pressure in a spray nozzle, or divided by centrifugal force in an appliance revolving at high speed. Atomization is preferable when roughly spherical particles are required. The temperature chosen for supply of the atomization system generally depends on its dispersal capacity. Preferably, it should be a temperature at which the molten sulphonate has a sufficiently low viscosity. In the case of the atomization of paraffin sodium sulphonates, for instance, the atomization system is supplied at a temperature of preferably between 150° and 200° C., since within this range the paraffin sodium sulphonates have a viscosity of between 100 and 50 poises.

The process according to the present invention is particularly useful for the treatment of untreated sulphonic solutions resulting from sulphoxidation of normal paraffins, the molecules of which contain between 7 and 30, and preferaly between 10 and 20 carbon atoms.

The invention is illustrated by, while not being confined to the follwing examples.

EXAMPLE 1

A photochemical reactor, supplied with a mixture of linear paraffins, and with water, sulphur dioxide and oxygen, produces an untreated sulphonic solution with the following composition in percentage weights:

| | |
|---|---|
| Sulphonic acid | 20.6% |
| Sulphuric acid | 7.2% |
| Non-sulphonated paraffins | 31% |
| Water | 41.2% |

After the gas has been removed from this solution, 300 g of heptanol are added to 1,000 g of it. The mixture is stirred in a contactor then directed to a decanting apparatus, where 340 g of heavy aqueous phase with 20% sulphuric acid separate out. The sulphonic acids contained in the organic light phase which also contains about 15% water are next neutralized by means of a 50% sodium hydroxide (12 N) solution, a slight excess compared with the stoichiometric quantity being used. An alcoholic solution of sodium sulphonate is obtained for which the ratio of the amount of water to the amount of heptanol is equal to about 0.6:1 (the corresponding ratio for the azeotrope between water and heptanol is equal to about 4.9:1).

The alcoholic solution of sodium sulphonate is conveyed to an evaporator functioning at 175° C., in which the heptanol and remaining water are separated out. The paraffin is then evaporated in a thin-layer evaporator, at sufficient temperature and pressure to remove all the paraffin.

226 g of sulphonate are obtained, containing approximately 2.5% sodium sulphate and less than 1% paraffin, said sulphonate being substantially anhydrous.

EXAMPLE 2

570 g of methanol are added to the organic phase described in Example 1, after separation of the sulphuric acid. Separation of the mixture occurs, into a paraffin phase more or less free of other products, and an alcohol phase containing the sulphonic acids in solution. The two phases are separated in a centrifugal machine.

302 g of paraffin are salted out and recycled to the photochemical reactor. The paraffin-free solution is neutralized with 61.5 g of 50% sodium hydroxide, then sent to a distillation column. The methanol is recovered at the top of the column, and recycled.

A heptanolic solution of sodium sulphonate showing a ratio of water amount to heptanol amount of about 0.28:1 is recovered at the bottom of the column and is sent to the evaporator, where the water, heptanol and remaining traces of paraffin are vaporized at sufficient temperatures and pressure for the sulphonate to be molten.

225 g of sulphonate are obtained after cooling, said sulphonate containing approximately 2.5% weight of sodium sulphonate, and being practically free from paraffin and substantially anhydrous.

EXAMPLE 3

600 g of methanol are added at atmospheric temperature to 1,000 g of the untreated sulphonic acid solution defined in Example 1. After stirring and decanting, the mixture separates into two phases, the upper one containing solely 300 g of paraffin, while the lower contains 10 g of paraffin, 72 g of sulphuric acid, 206 g of sulphonic acids, 412 g of water and 600 g of methanol.

The two phases are separated, and the paraffins are recycled to the photochemical reactor.

The methanol is removed from the methanol solution by conventional distillation.

210 g of heptanol are then added to the substantially paraffin-free solution of sulphonic acids and sulphuric acid, in order to salt out the sulphuric acid. The mixture passes into a contactor, and separates into two phases in a decanting apparatus.

The aqueous phase, containing 70 g of sulphuric acid, namely 97% of the sulphuric acid present in the reactor effluent, 300 g of water and less than 0.2% heptanol, is separated.

The organic phase, containing the sulphonic acids in solution and also about 20% by weight of water, is neutralized with 61.5 g of sodium hydroxide (12 N) and the neutralized solution for which the water to heptanol weight ratio is of about 0.75:1 is then sent to an evaporator for separation of the water and heptanol as described in example 2.

After cooling to atmospheric temperature, 227 g of a solid and substantially anhydrous substance are obtained, containing approximately 1.5% sodium sulphate and less than 1% paraffin.

EXAMPLE 4

300 g of 1-pentanol are added to 1,000 g of untreated sulphonic acid solution. After being stirred in a contactor, the mixture is sent to a decanting apparatus, where an aqueous phase is separated, containing 69.3 g of sulphuric acid, namely 92.2% of the sulphuric acid contained in the untreated sulphonic acid solution.

The organic phase, containing the sulphonic acids in solution, is then treated as in example 1, to isolate the sulphonic acid in the form of sodium sulphonate.

The sulphonate obtained contains approximately 1.8% sodium sulphate and 1% paraffin and is substantially anhydrous.

Use of quantities of 1-pentanol equal to 50 and 70% of the weight of untreated sulphonic acid solution results in salting-out in the aqueous phase of 96.7 and 90% respectively of the weight of sulphuric acid contained in the untreated solution.

EXAMPLE 5

The same method is followed as in example 1, and a series of treatments is performed in the untreated sulphonic acid solution, each time replacing the 1-heptanol with variable amounts of one of the following alcohols: 1-octanol, 2-ethylhexanol, 2-octanol, 1-dodecanol, 1-dodecanol, cyclohexanol, and a mixture of alcohols available commercially under the name "Alfol 610" (20 °% hexanol, 35% octanol and 44% decanol).

The sodium sulphate content of the sulphonate obtained is less than 4.5% weight when more than 90% sulphuric acid has been salted out in the aqueous phase, and is about 1.5% weight when approximately 97% of the sulfuric acid has been salted out. Further for the whole series of treatments the sulphonate recovered is substantially anhydrous.

EXAMPLE 6

For comparison purposes, two treatments are performed on the untreated sulphonic acid solution, one using isopropanol and the other 1-butanol. The amount of isopropanol used is 25% of the weight of untreated sulphonic acid solution, and the amount of 1-butanol is 50% of the weight of said untreated sulphonic acid solution.

When the mixture has been stirred and decanted, a sulphuric aqueous phase and an organic phase containing the sulphonic acids in solution are separated in each case. The aqueous phase Table

| Alcohol | % weight of alcohol in relation to untreated sulphonic acid solution | % sulphuric acid salted out in aqueous phase | water to alcohol weight in neutralized alcoholic phase |
|---|---|---|---|
| 1-octanol | 15 | 83.5 | 0.97 |
|  | 30 | 86.6 | 0.39 |
|  | 50 | 93.8 | 0.22 |
|  | 70 | 95.2 | 0.15 |
| 2-ethylhexanol | 15 | 89.9 | 0.92 |
|  | 30 | 91 | 0.36 |
|  | 50 | 96.7 | 0.20 |
|  | 70 | 97.3 | 0.14 |
| 2-octanol | 15 | 91 | 0.94 |
|  | 30 | 92.2 | 0.37 |
|  | 50 | 96.4 | 0.19 |
| 1-decanol | 15 | 91 | 0.92 |
|  | 30 | 93.7 | 0.38 |
|  | 50 | 96.7 | 0.20 |
|  | 70 | 96.3 | 0.15 |
| 1-dodecanol | 30 | 87.3 | 0.42 |
|  | 50 | 93.4 | 0.22 |
|  | 70 | 91.7 | 0.14 |
| Cyclohexanol | 30 | 92.9 | 0.45 |
|  | 50 | 91.8 | 0.27 |
|  | 70 | 89.9 | 0.21 |
| "Alfol" | 30 | 94 |  |
|  | 40 | 96.9 |  |
|  | 50 | 96.1 |  |

The above Table shows the percentage weights of sulphuric acid salted out in the aqueous phase depending on the type of alcohol, and the percentage weights in relation to the untreated sulphonic solution.

contains 30% by weight, in the case of isopropanol, and 60% by weight in the case of 1-butanol of the sulphuric acid contained in the untreated sulphonic acid solution.

In both cases the sulphuric acid content of the organic phase is too high for it to be possible to separate the sulphonic acids from it as described in earlier examples. The sulphuric acid remaining in the organic phase must first be separated in the form of sodium sulphate, with all the drawbacks this involves. In addition, the sodium sulphate content of the sulphonate is still about 4 to 5% weight.

Analysis of these examples shows that treatment of an untreated sulphonic acid solution with an alcohol containing 4 or fewer carbon atoms does not result in satisfactory separation of the sulphuric acid and sulphonic acids contained in the solution, and that in contrast, as has been found by the applicant, the use of alcohols with at least 5 carbon atoms in their molecule makes such separation possible, so that it is no longer necessary to separate the sulphuric acid in the form of sulphate, and the sulphate content of the sulphonate obtained is reduced.

EXAMPLE 7

The paraffin sulphonate obtained as described in example 3, resulting from treatment of an untreated sulphonic acid solution obtained by sulphoxidation of a fraction of paraffins containing from 13 to 17 carbon atoms, leaves the evaporator at a temperature of around 200° C., with a viscosity of about 50 poises.

The molten sulphonate is solidified on a drum cooled internally by circulating water. The flakes obtained with this drum are then ground in a disintegrator equipped with high-speed revolving blades.

The powder obtained is classified in a system of cyclones, and a fraction with particle-size of between 80 and 300 microns is separated, larger particles being returned to the disintegrator.

The sulphonate powder obtained is white, and is in the form of rounded grains. It is practically anhydrous, has high fluidity, and does not form lumps even after prolonged storage.

EXAMPLE 8

A crude aqueous paraffin sulphonic acid solution produced by sulphonating a $C_{13}$–$C_{17}$ paraffin fraction and having the following composition, in percentage by weight:

| Paraffin sulphonic acids | 30% |
|---|---|
| Sulphuric acid | 7% |
| Non-reacted paraffins | 1.5% |
| Water | 61.5% | has been treated as follows:

2.5 Kg of heptanol are added to 2.5 Kg of the crude solution. The mixture is stirred in a contacting vessel and then directed to a decanting apparatus, where 1.25 Kg of heavy aqueous phase containing substantially all the sulphuric acid separate out. After having decanted this aqueous phase, there remains 3.70 Kg of an organic phase containing the paraffin sulphonic acids in solution, said organic phase also containing about 12% by weight of water.

Using this organic solution of paraffin sulphonic acids three experiments were made as follows.

Experiment A (Processing the organic phase according to the invention)

1 KG of the organic solution has added thereto a 50% sodium hydroxide solution in a stoichiometric quantity to neutralize the sulphonic acids and to form the sodium sulphonate thereof. In the neutralized solution thus obtained the water to heptanol weight ratio amounted to about 0.24:1.

The neutralized solution was conveyed to an evaporator operating at 175° C., in which the heptanol and remaining water were distilled off. The paraffin was then evaporated in a thin layer evaporator at a temperature of 200° C. under a reduced pressure of 20 m m of Hg and 0.21 Kg of $C_{13}$–$C_{17}$ paraffin sodium sulphonate was recovered in the molten state, said sulphonate containing approximately 2.4% sodium sulfate and less than 1% paraffin.

The molten sulphonate thus recovered, which has a viscosity of about 50 poises, was solidified on a rotating drum with cooling water circulating inside, whereby flakes were obtained. The sodium sulphonate flakes were then crushed and a powder obtained consisting of particles with a diameter ranging from 200 to 400 microns.

This powder was white, anhydrous and free-flowing. No lumps were found to form after 20 days storage. Further, no foaming occurred during the evaporation of the neutralized organic phase.

Experiment B (Comparative test)

1 Kg of the solution of paraffin sulphonic acids in heptanol (organic phase) was heated in an evaporator operated at a temperature of 80° C. under a reduced pressure of 32 m m of Hg.

The solution which was not colored in the beginning of the operation quickly darkened and the sulphonic acids remaining after having distilled off all the volatile products contained in the solution were in the form of a black-colored viscous liquid.

After neutralization of this liquid with sodium hydroxide, evaporation of the neutralized solution to recover therefrom the sulphonate in the molten state, and transformation of the molten sulphonate into particles as indicated in experiment A, a tacky black sodium sulphonate powder was obtained, said powder being not suitable to be marketed for the applications involving particulate paraffin sulphonates.

Experiment C (Comparative test)

1 Kg of the solution of paraffin sulphonic acids in heptanol (organic phase) was contacted with a sufficient quantity of an aqueous sodium hydroxide solution to obtain after neutralization a neutralized phase wherein the water to heptanol weight ratio was equal to about 10:1 (the water to heptanol ratio for the azeotrope is equal to 4.9:1).

The neutralized solution was conveyed to an evaporator operating at 100° C. After a short time the sulphonate solution began to foam and a substantial amount of sulphonate was entrained by the water which distilled off after the azeotrope until distillation has been completed. It was not possible to evaporate the water remaining after distillation of the azeotrope without a considerable loss of sulphonate caused by said foaming.

From the results obtained in the comparative experiments A, B, and C it can be seen that in order to obtain a free-flowing anhydrous white sulphonate without loss of product it is critical that the organic phase is neutralized before being submitted to evaporation and also that in the neutralized solution submitted to evaporation, the water to slightly polar solvent (in this case heptanol) weight ratio does not exceed the value corresponding to the similar ratio for the azeotrope which forms between water and the slightly polar solvent.

What is claimed is:

1. A process for separating the sulphonic acids in an untreated paraffin sulphonic solution containing in addition to said paraffin sulphonic acids, sulphuric acid, water, and non-sulphonated paraffins, which comprises:
   (a) admixing with the paraffin sulphonic acid solution, at least one slightly polar alcohol selected from the group consisting of aliphatic and cycloaliphatic alcohols containing at least 5 carbon atoms, having a solubility in water less than 7% by weight which forms an azeotrope with water, thereby forming a mixture having an organic phase containing paraffin sulphonic acids dissolved therein and an aqueous phase containing the sulphuric acid;
   (b) separating said organic phase from said aqueous phase;
   (c) neutralizing said separated organic phase by admixture with a composition selected from the group consisting of alkali metal hydroxides, alkali metal carbonates, alkaline earth metal oxides, alkaline earth metal hydroxides, and alkaline earth metal carbonates thereby converting the sulphonic acids present in said organic phase into sulphonates, and forming a neutralized organic phase wherein the ratio of the amount of water to the amount of slightly polar alcohol in said neutralized phase is at most equal to the corresponding ratio for the azeotrope which forms between water and the slightly polar alcohol; and
   (d) removing the volatile components from the neutralized organic phase to recover the sulphonates under temperature and pressure conditions whereby said sulphonates are in a molten state.

2. A process according to claim 1, wherein from 10 to 150 parts by weight of said slightly polar alcohol is added per 100 parts by weight of said untreated paraffin sulphonic acid solution and said organic phase is neutralized with at least a stoichiometric amount of the selected alkali metal or alkaline earth metal compositions.

3. A process according to claim 1, wherein said slightly polar alcohol is added to said untreated sulphonic acid solution in an amount from about 30 to 100 parts by weight to 100 parts by weight of said untreated sulphonic acid solution.

4. A process according to claim 1, wherein said sulphonic acids are derived from normal paraffins having 7 to 30 carbon atoms.

5. A process according to claim 1, wherein said sulphonic acids are derived from normal paraffins having 10 to 20 carbon atoms.

6. A process according to claim 1, which includes the step of separating paraffins from said untreated sulphonic acid solution prior to the addition of said slightly polar alcohol thereto, by treating said solution with a water soluble polar liquid which does not mix with the paraffins and causes the separation thereof.

7. A process according to claim 1 wherein said molten sulphonate mass is cooled into flakes, which are then ground to the required particle size.

8. A process according to claim 1 wherein the water solubility of the slightly polar alcohol is less than 5% by weight.

9. A process according to claim 1, wherein said slightly polar alcohol contains from 5 to 12 carbon atoms and has a solubility in water less than 5% by weight.

10. The process of claim 1 wherein the molten sulphonate is cooled and comminuted into particulate form.

* * * * *

UNITED STATES PATENT AND TRADEMARK OFFICE
CERTIFICATE OF CORRECTION

PATENT NO. : 4,177,208
DATED : December 4, 1979
INVENTOR(S) : Aristide Boy, et al It is certified that error appears in the above—identified patent and that said Letters Patent is hereby corrected as shown below:

In the title page, the name of the Assignee should read
--ATO CHIMIE--.

In the Abstract, line 3: "sulphonic acid" should be
--sulphuric acid--.

Column 1, line 46: "sulphuric acids" should be
--sulphuric acid--.

Column 5, line 21: "preferaly" should be --preferably--.

Column 7, line 10: "°%" should be --%--.

Column 9, line 62: "solvent" should be --alcohol--.

line 65: "solvent" should be --alcohol--.

Signed and Sealed this

Thirteenth Day of May 1980

[SEAL]

Attest:

SIDNEY A. DIAMOND

Attesting Officer  Commissioner of Patents and Trademarks